(12) United States Patent
Agnew

(10) Patent No.: US 10,143,457 B2
(45) Date of Patent: Dec. 4, 2018

(54) FISTULA PLUGS HAVING INCREASED COLUMN STRENGTH AND FISTULA PLUG DELIVERY APPARATUSES AND METHODS

(75) Inventor: Charles W. Agnew, West Lafayette, IN (US)

(73) Assignee: Cook Biotech Incorporated, West Lafayette, IN (US)

( * ) Notice: Subject to any disclaimer, the term of this patent is extended or adjusted under 35 U.S.C. 154(b) by 1573 days.

(21) Appl. No.: 12/098,701

(22) Filed: Apr. 7, 2008

(65) Prior Publication Data

US 2008/0245374 A1 Oct. 9, 2008

Related U.S. Application Data

(60) Provisional application No. 60/910,509, filed on Apr. 6, 2007.

(51) Int. Cl.
*A61B 17/00* (2006.01)
*A61B 17/12* (2006.01)
(Continued)

(52) U.S. Cl.
CPC .... *A61B 17/0057* (2013.01); *A61B 17/12159* (2013.01); *A61B 17/3431* (2013.01);
(Continued)

(58) Field of Classification Search
CPC .......... A61B 17/0057; A61B 17/12159; A61B 2090/00004; A61B 2017/00641;
(Continued)

(56) References Cited

U.S. PATENT DOCUMENTS 2,127,903 A 8/1938 Bowen
4,511,653 A 4/1985 Play et al.
(Continued)

FOREIGN PATENT DOCUMENTS

EP 1010396 6/2000
EP 1188414 3/2002
(Continued)

OTHER PUBLICATIONS

Himpson, Rebecca C., et al. "Histological evidence for enhanced anal fistula repair using autologous fibroblasts in a dermal collagen matrix". Comparative Clinical Pathology, Apr. 2006, vol. 16, No. 1.
(Continued)

*Primary Examiner* — Victoria J Hicks
(74) *Attorney, Agent, or Firm* — Woodard, Emhardt, Moriarty, McNett & Henry LLP

(57) ABSTRACT

The present invention provides, in certain aspects, medical devices deliverable into passageways and other open spaces in the body. In one embodiment, the invention provides a fistula plug for delivery into a fistula tract. This fistula plug includes an elongate plug body, and a removable core material that is received in the plug body and effective to increase the column strength of the plug body. The plug body may be formed with one or more of a variety of biocompatible materials including some that are naturally derived and some that are non-naturally derived. The present invention also provides apparatuses and methods for delivering these and other medical devices into the body. One such apparatus includes a fistula plug having a plug body, and a removable delivery device received in the plug body, wherein the delivery device is effective to deliver the plug body into a fistula tract when advanced therethrough.

51 Claims, 4 Drawing Sheets

(51) Int. Cl.
 *A61B 17/34* (2006.01)
 *A61B 90/00* (2016.01)
(52) U.S. Cl.
 CPC .............. *A61B 2017/00004* (2013.01); *A61B 2017/00336* (2013.01); *A61B 2017/00641* (2013.01); *A61B 2017/00654* (2013.01); *A61B 2017/1205* (2013.01); *A61B 2090/037* (2016.02)
(58) Field of Classification Search
 CPC .. A61B 2017/00654; A61B 2017/1205; A61B 2017/00575; A61B 2017/00301; A61B 2017/00623; A61B 2017/00336; A61B 17/12031; A61B 17/12036; A61B 17/12022; A61B 17/1204; A61B 17/12027; A61F 9/00772; A61F 6/146; A61F 6/20
 USPC .......................................... 128/887; 606/191
 See application file for complete search history.

(56) References Cited

U.S. PATENT DOCUMENTS

| | | | |
|---|---|---|---|
| 4,902,508 A | 2/1990 | Badylak et al. | |
| 4,956,178 A | 9/1990 | Badylak et al. | |
| 4,981,465 A | 1/1991 | Ballan | |
| 5,192,302 A | 3/1993 | Kensey et al. | |
| 5,222,970 A | 6/1993 | Reeves | |
| 5,275,826 A | 1/1994 | Badylak et al. | |
| 5,281,422 A | 1/1994 | Badylak et al. | |
| 5,304,123 A | 4/1994 | Atala et al. | |
| 5,334,216 A | 8/1994 | Vidal | |
| 5,374,261 A | 12/1994 | Yoon | |
| RE34,866 E | 2/1995 | Kensey | |
| 5,411,475 A | 5/1995 | Atala et al. | |
| 5,423,777 A * | 6/1995 | Tajiri et al. ................... | 604/294 |
| 5,516,533 A | 5/1996 | Badylak et al. | |
| 5,554,389 A | 9/1996 | Badylak et al. | |
| 5,584,827 A | 12/1996 | Korteweg | |
| 5,620,461 A | 4/1997 | Muijs Van De Moer | |
| 5,628,762 A | 5/1997 | Moshin | |
| 5,643,305 A | 7/1997 | Moshin | |
| 5,752,974 A | 5/1998 | Rhee | |
| 5,755,791 A | 5/1998 | Whitson et al. | |
| 5,779,672 A | 7/1998 | Dormandy | |
| 5,830,228 A | 11/1998 | Knapp et al. | |
| 5,955,110 A | 9/1999 | Patel et al. | |
| 5,993,844 A | 11/1999 | Abraham et al. | |
| 5,997,575 A | 12/1999 | Whitson et al. | |
| 6,013,853 A | 1/2000 | Athanasiou et al. | |
| 6,090,996 A | 7/2000 | Li | |
| 6,099,567 A | 8/2000 | Badylak et al. | |
| 6,126,686 A | 10/2000 | Badylak et al. | |
| 6,165,193 A * | 12/2000 | Greene et al. ................ | 606/191 |
| 6,206,931 B1 | 3/2001 | Cook et al. | |
| 6,220,336 B1 | 3/2001 | Badylak et al. | |
| 6,315,787 B1 | 11/2001 | Tsugita | |
| 6,375,989 B1 | 4/2002 | Badylak et al. | |
| 6,569,081 B1 | 5/2003 | Nielsen | |
| 6,666,892 B2 | 12/2003 | Hiles et al. | |
| 7,204,253 B2 * | 4/2007 | Mendius ............ | A61B 17/0057 128/846 |
| 8,083,768 B2 | 12/2011 | Ginn et al. | |
| 2003/0013989 A1* | 1/2003 | Obermiller et al. .......... | 600/567 |
| 2003/0036797 A1 | 2/2003 | Malaviya et al. | |
| 2003/0051735 A1 | 3/2003 | Pavcnik et al. | |
| 2004/0158185 A1 | 8/2004 | Moran et al. | |
| 2005/0013844 A1 | 1/2005 | Hadlock et al. | |
| 2005/0049826 A1 | 3/2005 | Burgard | |
| 2005/0070759 A1 | 3/2005 | Armstrong | |
| 2005/0155608 A1 | 7/2005 | Pavcnik et al. | |
| 2005/0159776 A1 | 7/2005 | Armstrong | |
| 2005/0182495 A1 | 8/2005 | Perrone | |
| 2005/0216016 A1* | 9/2005 | Contiliano .......... | A61B 17/864 606/916 |
| 2006/0015142 A1 | 1/2006 | Malazgirt | |
| 2007/0004961 A1 | 1/2007 | Case et al. | |
| 2007/0198059 A1* | 8/2007 | Patel et al. .................... | 606/213 |
| 2008/0004657 A1* | 1/2008 | Obermiller et al. .......... | 606/213 |
| 2008/0027477 A1* | 1/2008 | Obermiller et al. .......... | 606/191 |
| 2008/1002747 | 1/2008 | Obermiller et al. | |

FOREIGN PATENT DOCUMENTS

| | | |
|---|---|---|
| RU | 2180529 C2 | 3/2002 |
| SU | 1673130 A1 | 8/1991 |
| SU | 1690737 A1 | 11/1991 |
| SU | 1718837 | 3/1992 |
| WO | WO 98/11846 | 3/1998 |
| WO | WO 98/25637 | 6/1998 |
| WO | WO 00/19912 | 4/2000 |
| WO | WO 00/72759 | 12/2000 |
| WO | WO 05/020847 | 3/2005 |
| WO | WO 2005/020823 A1 | 3/2005 |
| WO | WO 05/053547 | 6/2005 |
| WO | WO 05/070302 | 8/2005 |
| WO | WO 06/119256 | 11/2006 |
| WO | WO 07/011443 | 1/2007 |
| WO | WO 2007/002260 | 1/2007 |
| WO | WO 2007/064819 A2 | 8/2007 |
| WO | WO 2007/090150 A2 | 8/2007 |
| WO | WO 2007/090155 A1 | 8/2007 |

OTHER PUBLICATIONS

Khairy, G. E. A., et al. "Percutaneous obliteration of duodenal fistula". J.R. Coll. Surg. Edinb., 45, Oct. 2000, 342-344.

Lisle, David A., et al. "Percutaneous Gelfoam Embolization of Chronic Enterocutaneous Fistulas: Report of Three Cases". Diseases of the Colon & Rectum, vol. 50, No. 2, Dec. 2006.

Maluf-Fiho, F. et al. "Enscopic Treatment of Esophagogastric Fistulae with an Acellular Matrix" Gastrointestinal Endoscopy, Elsevier, NL, vol. 59, No. 5, Apr. 2004 (Apr. 2004), p. 151, XP004854594 abstract.

Miklos, J.R., et al. "Rectovaginal Fistula Repair Utilizng a Cadaveric Dermal Allograft", International Urogynecology Journal, 1999, vol. 10, No. 6, pp. 405-406.

Moore, Robert D., et al. "Rectovaginal Fistula Repair Using a Porcine Dermal Graft". Obstetrics & Gynecology, 2004, 104, 1165-1167.

Schultz, Daivd J., et al. "Procine Small Intestine Submucosa as a Treatment for Enterocutaneous Fistulas", Journal of American College of Surgeons, 2002, vol. 194, No. 4, Apr. 2002, pp. 541-543.

Schwesinger, Wayne H., "Management of Persistent Fistula After Gastrectomy" on-line question (www.medscape.com), posted on May 14, 2002.

Shah, A.M., et al. "Bronchoscopic closure of bronchopleural fistula using gelfoam" abstact. Journal of Association of Physicians of India, 2004, vol. 52 n JUIN, pp. 508-509.

Shaker MA, Hindy AM, Mounir RM, Geaisa KM. Egypt Dent J. Jul. 1995; 41(3): 1237-42.

Sheiman, Robert G., et al. "Percutaneous Treatment of a Pancreatic Fistula after Pancreaticoduodenectomy". J Vasc Interv Radiol, 2001, vol. 12, No. 4, pp. 524-526.

Shelton, Andrew A., et al. Transperineal Repair of Persistent Rectovaginal Fistulas Using an Acellular Cadaveric Dermal Grant (AlloDerm®). Diseases of the Colon & Rectum, Sep. 2006, vol. 49, No. 9.

Wilson Gunn on behalf of unnamed party, Letter to the European Patent Office, Jan. 30, 2007, pp. 1-4.

U.S. Appl. No. 12/793,030 to F. Joseph Obermiller et. al., Office Action dated May 14, 2015.

U.S. Appl. No. 11/415,403 to Obermiller et al., Office Action dated May 19, 2015.

* cited by examiner

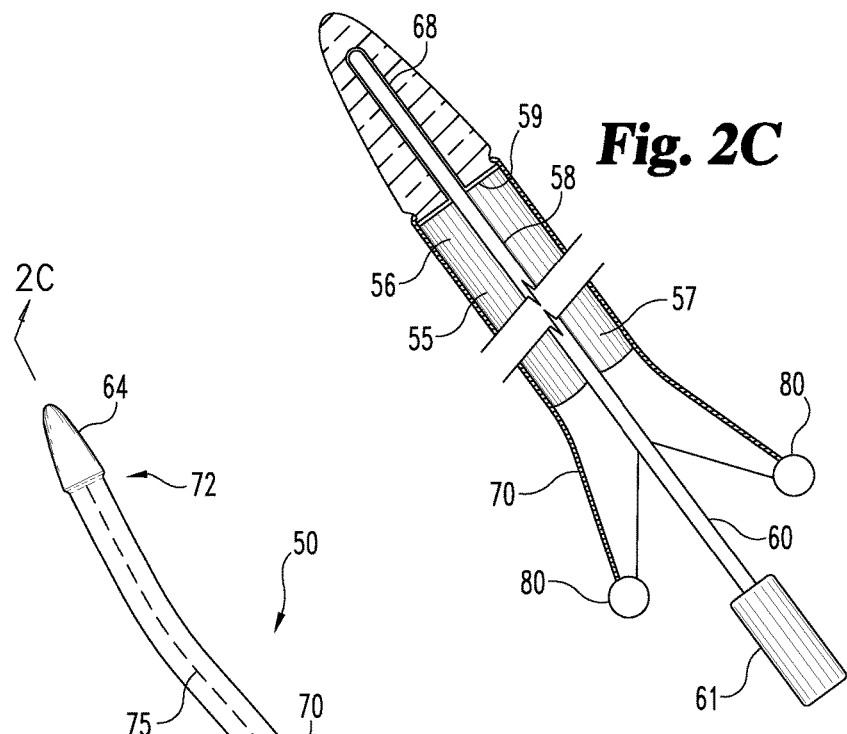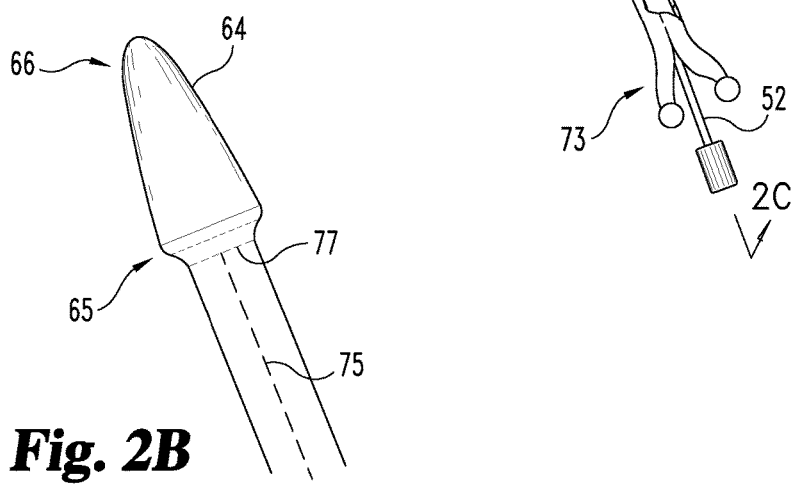

FISTULA PLUGS HAVING INCREASED COLUMN STRENGTH AND FISTULA PLUG DELIVERY APPARATUSES AND METHODS

REFERENCE TO RELATED APPLICATION

The present application claims the benefit of U.S. Provisional Patent Application Ser. No. 60/910,509 filed Apr. 6, 2007 entitled FISTULA PLUGS HAVING INCREASED COLUMN STRENGTH AND FISTULA PLUG DELIVERY APPARATUSES AND METHODS which is hereby incorporated by reference in its entirety.

BACKGROUND

The present invention relates generally to medical devices and in particular aspects to devices and methods for plugging fistulae and other passageways in the body.

As further background, there exist a variety of passages and other open spaces in the body that can be plugged or otherwise filled to provide benefit to the patient. For example, it may be desirable to occlude an open space in the vasculature (e.g., a blood vessel lumen). In some instances, a device is deployed within the venous system, e.g., within the greater and/or lesser saphenous vein, to treat varicose veins and other conditions.

As well, it may be desirable to plug or otherwise fill a fistula. A variety of fistulae can occur in humans, and they can occur for a variety of reasons including but not limited to as a congenital defect, as a result of inflammatory bowel disease, such as Chron's disease, irradiation, trauma, such as childbirth, and as a side effect from a surgical procedure. Further, several different types of fistulae can occur, for example, urethro-vaginal fistulae, vesico-vaginal fistulae, tracheo-esophageal fistulae, enterocutaneous fistulae including gastro-cutaneous fistulae, and any number of anorectal fistulae, such as recto-vaginal fistula, recto-vesical fistulae, recto-urethral fistulae, or recto-prostatic fistulae.

The path which fistulae take, and their complexity, can vary. A fistula may take a take a "straight line" path from a primary opening to a secondary opening, known as a simple fistula. Alternatively, a fistula may comprise multiple tracts ramifying from a primary opening and have multiple secondary openings. This is known as a complex fistula.

Anorectal fistulae can result from infection in the anal glands, which are located around the circumference of the distal anal canal that forms the anatomic landmark known as the dentate line. Approximately 20-40 such glands are found in humans. Infection in an anal gland can result in an abscess. This abscess then can track through soft tissues (e.g., through or around the sphincter muscles) into the perianal skin, where it drains either spontaneously or surgically. The resulting void through soft tissue is known as a fistula. The internal or inner opening of the fistula, usually located at or near the dentate line, is known as the primary opening. Any external or outer openings, which are usually located in the perianal skin, are known as secondary openings.

One technique for treating a perianal fistula is to make an incision adjacent the anus until the incision contacts the fistula and then excise the fistula from the anal tissue. This surgical procedure tends to sever the fibers of the anal sphincter, and may cause incontinence. Other surgical treatment of fistulae involve passing a fistula probe through the tract of the fistula in a blind manner, using primarily only tactile sensation and experience to guide the probe. Having passed the probe through the fistula tract, the overlying tissue is surgically divided. This is known as a fistulotomy. Since a variable amount of sphincter muscle is divided during the procedure, fistulotomy also may result in impaired sphincter control, and even frank incontinence.

A gastrointestinal fistula is an abnormal passage that leaks contents of the stomach or the intestine (small or large bowel) to other organs, usually other parts of the intestine or the skin. For example, gastrojejunocolic fistulae include both enterocutaneous fistulae (those occurring between the skin surface and the intestine, namely the duodenum, the jejunum, and the ileum) and gastric fistulae (those occurring between the stomach and skin surface). Another type of fistula occurring in the gastrointestinal tract is an enteroenteral fistula, which refers to a fistula occurring between two parts of the intestine. Gastrointestinal fistulae can result in malnutrition and dehydration depending on their location in the gastrointestinal tract. They can also be a source of skin problems and infection. The majority of these types of fistulae are the result of surgery (e.g., bowel surgery), although sometimes they can develop spontaneously or from trauma, especially penetrating traumas such as stab wounds or gunshot wounds. Inflammatory processes, such as infection or inflammatory bowel disease (Crohn's disease), may also cause gastrointestinal fistulae. In fact, Crohn's disease is the most common primary bowel disease leading to enterocutaneous fistulae, and surgical treatment may be difficult because additional enterocutaneous fistulae develop in many of these patients postoperatively.

Treatment options for gastrointestinal fistulae vary. Depending on the clinical situation, patients may require IV nutrition and a period of time without food to allow the fistula time to close on its own. Indeed, nonsurgical therapy may allow spontaneous closure of the fistula, although this can be expected less than 30% of the time according to one estimate. A variable amount of time to allow spontaneous closure of fistulae has been recommended, ranging from 30 days to 6 to 8 weeks. During this preoperative preparation, external control of the fistula drainage prevents skin disruption and provides guidelines for fluid and electrolyte replacement. In some cases, surgery is necessary to remove the segment of intestine involved in a non-healing fistula.

When surgery is deemed necessary, one operation for fistula closure is resection of the fistula-bearing segment and primary end-to-end anastomosis. The anastomosis may be reinforced by greater omentum or a serosal patch from adjacent small bowel. Still other methods for treating fistulae involve injecting sclerosant or sealant (e.g., collagen or fibrin glue) into the tract of the fistula to block the fistula. Closure of a fistula using a sealant is typically performed as a two-stage procedure, including a first-stage seton placement and injection of the fibrin glue several weeks later. This allows residual infection to resolve and to allow the fistula tract to "mature" prior to injecting a sealant. If sealant or sclerosant were injected as a one-stage procedure, into an "unprepared" or infected fistula, this may cause a flare-up of the infection and even further abscess formation.

There remain needs for improved and/or alternative devices and methods for plugging open spaces in the body. The present invention is addressed to those needs.

SUMMARY

The present invention provides, in certain aspects, unique medical devices for delivery into passageways and other similar open spaces in the body. In some cases, these devices incorporate or are otherwise associated with an object that enhances the delivery characteristics of the device. The invention also provides apparatuses and methods for delivering these and other medical devices into the body. Some inventive apparatuses are configured for delivering a fistula plug into a fistula tract. One such apparatus comprises a fistula plug having a plug body, and a removable delivery device received in the plug body, wherein the delivery device is effective to deliver the plug body into a fistula tract when advanced therethrough. The delivery device may be received in the plug body in a variety of fashions including some that enable the delivery device to push and/or pull the plug body through the fistula tract. The delivery device can exhibit any suitable size, shape and configuration for receipt in the plug body and for delivering the plug body into the fistula tract. As well, the delivery device can be positioned at any suitable location in the plug body. Although not necessary to broader aspects of the invention, some plug bodies provide a designated opening (e.g., a lumen or other passage) into which a delivery device can be positioned. In one aspect, a lumen extends through a plug body from a first plug body surface to a second plug body surface, and a delivery device, which extends through the plug body lumen, has a leading tip configured to remain forward of the plug body when the delivery device is advanced through the fistula tract. Further, some inventive apparatuses include a protective sheath positioned around the plug body.

In another embodiment, the invention provides a method for delivering a fistula plug into a fistula tract, which utilizes a delivery apparatus such as that described above. This method includes advancing the delivery device through the fistula tract, wherein the plug body is delivered into the fistula tract. In some aspects, the delivery apparatus is configured such that advancing the delivery device through the fistula tract pulls the plug body through the fistula tract, while in other aspects, it is configured such that advancing the delivery device through the fistula tract pushes the plug body through the fistula tract. Additionally, the delivery apparatus may be configured such that a portion of the plug body is positioned forward of the delivery device as the delivery device is advanced through the fistula tract, although in some forms, it is configured such that no portion of the plug body is positioned forward of the delivery device as the delivery device is advanced through the fistula tract.

Another aspect of the present invention provides a fistula plug for delivery into a fistula tract. This fistula plug comprises an elongate plug body, and a removable core material that is received in the plug body and effective to increase the column strength of the plug body. The plug body can exhibit any suitable size, shape and configuration for delivery into a fistula tract, and in some embodiments, the plug body, or a portion thereof, will include a generally cylindrical and/or a generally conical portion. As well, the plug body may be formed with one or more of a variety of biocompatible materials including some that are naturally derived and some that are non-naturally derived. In a preferred embodiment, the plug body is comprised of a remodelable, angiogenic material, for example, a remodelable extracellular matrix material such as submucosa. Further, the removable core material can be shaped and configured in a variety of fashions, and may be comprised of any suitable material including any of those used in forming the plug body. In certain aspects, the core material is formed with a synthetic, polymeric material that is somewhat flexible.

Other objects, embodiments, forms, features, advantages, aspects, and benefits of the present invention shall become apparent from the detailed description and drawings included herein.

BRIEF DESCRIPTION OF THE DRAWINGS

FIG. 2A provides a side view of another fistula plug delivery apparatus of the present invention.

FIG. 2B is an enlarged, partial view of the fistula plug delivery apparatus of FIG. 2A.

FIG. 2C is an enlarged, cross-sectional view of the fistula plug delivery apparatus of FIG. 2A along the view line 2C—2C shown in FIG. 2A.

DETAILED DESCRIPTION

Figure 1:
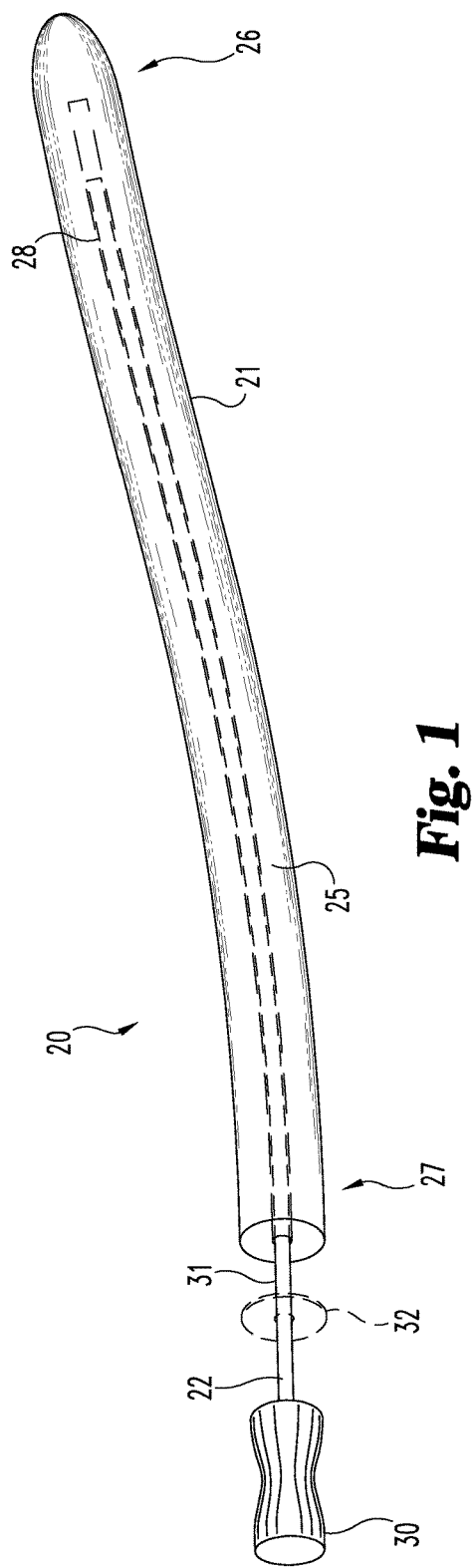
FIG. 1 is a perspective view of a fistula plug delivery apparatus according to one embodiment of the present invention.

While the present invention may be embodied in many different forms, for the purpose of promoting an understanding of the principles of the present invention, reference will now be made to the embodiments illustrated in the drawings, and specific language will be used to describe the same. It will nevertheless be understood that no limitation of the scope of the invention is thereby intended. Any alterations and further modifications in the described embodiments and any further applications of the principles of the present invention as described herein are contemplated as would normally occur to one skilled in the art to which the invention relates.

As disclosed above, in certain aspects, the present invention provides unique medical devices deliverable into the body to provide treatment. Some of these devices are fistula plugs for delivery into a fistula tract. In one embodiment, an inventive device includes a plug body, and a removable object positioned in the plug body. An object of this sort, when combined with the plug body, can alter certain structural and/or other characteristics of the plug body including at least some of those relating to its ability to be delivered into and through a fistula tract. Illustratively, an inventive plug of this sort can comprise an elongate plug body, and a removable core material positioned in the body, wherein the added core material is effective to increase the column strength of the plug body. In some instances, such an increase in column strength will enable the plug body to be pushed into and through a fistula tract where it would have been somewhat more difficult or even impossible to be so pushed without the core material.

The invention also provides various apparatuses and methods for delivering these and other medical devices into the body. Some of these apparatuses combine a fistula plug and a delivery device useful in delivering the plug into a fistula tract. One such apparatus includes a fistula plug having a plug body, and a removable delivery device received in the plug body, wherein the delivery device is effective to deliver the plug body into a fistula tract when advanced therethrough. For example and referring now to FIG. 1, shown is a fistula plug delivery apparatus 20 according to the present invention. Apparatus 20 includes a fistula plug 21 and a removable delivery device 22. Fistula plug 21 is comprised of a plug body 25 having a distal portion 26 and a proximal portion 27. A central lumen 28 extends through plug body 25 along its length. Lumen 28 does not extend entirely through plug body 25, but rather terminates at a transverse wall portion in an area proximate distal portion 26. A fistula plug such as plug 21 may be formed with one or more of a variety of materials, and can be sized and adapted for delivery into a variety of fistula tracts as discussed elsewhere herein. In this specific illustrative embodiment, plug body 25 is formed with a somewhat pliable, collagen-containing material, e.g., a remodelable collagenous material derived from a warm-blooded mammal.

Delivery device 22 includes a handle 30 and an elongate delivery member 31 extending from this handle. Delivery member 31 is sized and configured for receipt in plug body lumen 28, and can be advanced through the lumen to an area at or near its distal terminus. In some embodiments involving an apparatus of this sort, the delivery member can be advanced through the lumen until a transverse delivery surface at a distal end of the delivery member contacts the plug body wall defining this lumen terminus. Such contact can provide a counterforce when pushing plug body 25 through a body passageway with delivery device 22. If necessary and/or desirable, such a plug body wall may be strengthened or otherwise reinforced in an effort to prevent the distal end of delivery member 31 from piercing through the wall during delivery, for example, by incorporating a reinforcing material into the plug body at this location and/or advantageously altering the existing plug body material at this location to provide reinforcement.

Delivery device 22 also includes a transverse delivery surface such as an optional disc-shaped member 32, which is fixedly positioned along delivery member 31 for contacting a transverse wall portion at a plug body proximal portion 27 when delivery member 31 is sufficiently advanced through plug body lumen 28. Such contact can provide a counterforce when pushing plug body 25 through a fistula tract with delivery device 22. In this embodiment, disc-shaped member 32 has roughly the same diameter as plug body 25, thus providing a generally even load distribution across plug body proximal portion 27 when disc-shaped member 32 is applied thereto. In some forms, such a disc-shaped member is translatable along delivery member 31.

Accordingly, delivery apparatus 20 can be used in delivering fistula plug 21 into a fistula tract. Illustratively, with plug body 25 received over delivery member 31, an operator can grip handle 30, and insert plug body distal portion 26 into a fistula tract through a fistula opening (e.g., a secondary opening). Thereafter, delivery device 22 can be further advanced through the tract toward another fistula opening (e.g., a primary opening), wherein plug body 25 is forced through the tract by delivery device 22, e.g., by the distal end of delivery member 31 contacting a portion of the plug body wall at the distal terminus of lumen 28 and/or by disc-shaped member 32 contacting plug body proximal portion 27 as the device is advanced. In addition to what is shown, plug body distal portion 26 may be shaped and configured in a variety of manners to enhance the travel of apparatus 20 into and through the tract. In some forms, distal portion 26 is configured to have one or more physical, chemical, biological and/or other properties differing from those of other regions of the plug body. And in this regard, distal portion 26 may be formed with a different material than the remainder of the plug body, or it may be formed with the same material but be chemically or otherwise altered, e.g., to make distal portion 26 relatively more dense than other portions of the plug body. In some forms, all or a portion of a plug body may be formed with a lubricious material and/or coated with a lubricious coating material to enhance its ability to travel in the body.

Delivery device 22 can be advanced any suitable distance through the tract to desirably position plug body 25 therein, for example, with fistula plug distal portion 26 positioned at or near a primary fistula opening. Then, delivery device 22 can be simultaneously withdrawn back through the fistula tract and removed from plug body 25, leaving the plug body in the tract. In some cases, impingement of the plug body by tissues surrounding the fistula may be enough to keep the plug body in the tract as the delivery device is being removed. Nonetheless, it may be necessary and/or desirable to hold plug body 25 in place in the fistula tract (e.g., directly by hand or indirectly using a tool) while removing delivery device 22 therefrom so as to maintain desirable positioning of the plug in the tract. Illustratively, a component similar to disc-shaped member 32 or another suitable device component can be adapted to translate along delivery member 31, and in this regard, may be a used to provide a counterforce against the plug body when delivering the plug into the tract and when removing the delivery device from the plug. Such a member can be moved into position and held against plug body proximal portion 27 when forcing the plug into the tract. As well, such a member can be held against plug body proximal portion 27 as delivery member 31 is withdrawn from the plug.

While removable objects such as delivery device 22 can be removed from a graft after the graft is implanted in the body, in some instances, all or a portion of an otherwise removable object will remain in the graft indefinitely or for a certain period of time following implantation. Where only a portion of a removable device is to remain in the graft following implantation, this portion may be separated from those portions being removed in a variety of manners including but not limited to by cutting, breaking, etc. In some instances, a removable device will include one or more adaptations for facilitating this sort of separation. Suitable adaptations will be recognized by the skilled artisan, and therefore, are encompassed by the present invention. Illustratively, a removable object can incorporate scores, thinner portions, and other adaptations that weaken a portion of the object to facilitate a break-away operation in separating a portion to be removed. Such a weakened portion may include any suitable means for facilitating breaking or otherwise separating along the device. Any portion of a removable device that is to remain in the graft following implantation can be coupled to, bonded to, or otherwise fixed to the graft and/or patient tissue at the treatment area to maintain this portion in the graft, although in some instances, friction may be enough to keep the portion desirably seated. Also, portions of a removable device that are to remain in a graft following implantation can be formed with one or more of a variety of materials including, in some cases, naturally derived and non-naturally derived resorbable materials.

Turning now to a more detailed discussion of materials useful in forming plugging devices of the invention, such a device, or any component thereof, may be formed with one or more of a variety of biocompatible materials including some that are naturally derived and some that are non-naturally derived. In advantageous embodiments, these devices are comprised of a remodelable material. Particular advantage can be provided by plug members including a remodelable collagenous material. Such remodelable collagenous materials, whether reconstituted or non-reconstituted, can be provided, for example, by collagenous materials isolated from a warm-blooded vertebrate, and especially a mammal. Such isolated collagenous material can be processed so as to have remodelable, angiogenic properties and promote cellular invasion and ingrowth. Remodelable materials may be used in this context to promote cellular growth on, around, and/or within tissue in which a plugging device of the invention is implanted, e.g., around tissue defining a fistula tract, an opening to a fistula, or another space in the body.

Suitable remodelable materials can be provided by collagenous extracellular matrix (ECM) materials possessing biotropic properties. For example, suitable collagenous materials include ECM materials such as those comprising submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa including small intestinal submucosa, stomach submucosa, urinary bladder submucosa, and uterine submucosa. Collagenous matrices comprising submucosa (potentially along with other associated tissues) useful in the present invention can be obtained by harvesting such tissue sources and delaminating the submucosa-containing matrix from smooth muscle layers, mucosal layers, and/or other layers occurring in the tissue source. For additional information as to some of the materials useful in the present invention, and their isolation and treatment, reference can be made, for example, to U.S. Pat. Nos. 4,902,508, 5,554,389, 5,993,844, 6,206,931, and 6,099,567.

Submucosa-containing or other ECM tissue used in the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of any ECM tissue used in the present invention.

A typical layer thickness for an as-isolated submucosa or other ECM tissue layer used in the invention ranges from about 50 to about 250 microns when fully hydrated, more typically from about 50 to about 200 microns when fully hydrated, although isolated layers having other thicknesses may also be obtained and used. These layer thicknesses may vary with the type and age of the animal used as the tissue source. As well, these layer thicknesses may vary with the source of the tissue obtained from the animal source.

Suitable bioactive agents may include one or more bioactive agents native to the source of the ECM tissue material. For example, a submucosa or other remodelable ECM tissue material may retain one or more growth factors such as but not limited to basic fibroblast growth factor (FGF-2), transforming growth factor beta (TGF-beta), epidermal growth factor (EGF), cartilage derived growth factor (CDGF), and/or platelet derived growth factor (PDGF). As well, submucosa or other ECM materials when used in the invention may retain other native bioactive agents such as but not limited to proteins, glycoproteins, proteoglycans, and glycosaminoglycans. For example, ECM materials may include heparin, heparin sulfate, hyaluronic acid, fibronectin, cytokines, and the like. Thus, generally speaking, a submucosa or other ECM material may retain one or more bioactive components that induce, directly or indirectly, a cellular response such as a change in cell morphology, proliferation, growth, protein or gene expression.

Submucosa or other ECM materials of the present invention can be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with appropriate staining. Such non-collagenous solids can constitute a significant percentage of the dry weight of the ECM material in certain inventive embodiments, for example at least about 1%, at least about 3%, and at least about 5% by weight in various embodiments of the invention.

The submucosa or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the formation of new blood vessels into the materials. Methods for measuring in vivo angiogenesis in response to biomaterial implantation have recently been developed. For example, one such method uses a subcutaneous implant model to determine the angiogenic character of a material. See, C. Heeschen et al., Nature Medicine 7 (2001), No. 7, 833-839. When combined with a fluorescence microangiography technique, this model can provide both quantitative and qualitative measures of angiogenesis into biomaterials. C. Johnson et al., Circulation Research 94 (2004), No. 2,262-268.

Further, in addition or as an alternative to the inclusion of such native bioactive components, non-native bioactive components such as those synthetically produced by recombinant technology or other methods (e.g., genetic material such as DNA), may be incorporated into an ECM material. These non-native bioactive components may be naturally-derived or recombinantly produced proteins that correspond to those natively occurring in an ECM tissue, but perhaps of a different species. These non-native bioactive components may also be drug substances. Illustrative drug substances that may be added to materials include, for example, anti-clotting agents, e.g. heparin, antibiotics, anti-inflammatory agents, thrombus-promoting substances such as blood clotting factors, e.g., thrombin, fibrinogen, and the like, and anti-proliferative agents, e.g. taxol derivatives such as paclitaxel. Such non-native bioactive components can be incorporated into and/or onto ECM material in any suitable manner, for example, by surface treatment (e.g., spraying) and/or impregnation (e.g., soaking), just to name a few. Also, these substances may be applied to the ECM material in a premanufacturing step, immediately prior to the procedure (e.g., by soaking the material in a solution containing a suitable antibiotic such as cefazolin), or during or after engraftment of the material in the patient.

Plug members of the invention can include xenograft material (i.e., cross-species material, such as tissue material from a non-human donor to a human recipient), allograft material (i.e., interspecies material, with tissue material from a donor of the same species as the recipient), and/or autograft material (i.e., where the donor and the recipient are the same individual). Further, any exogenous bioactive substances incorporated into an ECM material may be from the same species of animal from which the ECM material was derived (e.g. autologous or allogenic relative to the ECM material) or may be from a different species from the ECM material source (xenogenic relative to the ECM material). In certain embodiments, ECM material will be xenogenic relative to the patient receiving the graft, and any added exogenous material(s) will be from the same species (e.g. autologous or allogenic) as the patient receiving the graft. Illustratively, human patients may be treated with xenogenic ECM materials (e.g. porcine-, bovine- or ovine-derived) that have been modified with exogenous human material(s) as described herein, those exogenous materials being naturally derived and/or recombinantly produced.

ECM materials used in the invention may be essentially free of additional, non-native crosslinking, or may contain additional crosslinking. Such additional crosslinking may be achieved by photo-crosslinking techniques, by chemical crosslinkers, or by protein crosslinking induced by dehydration or other means. However, because certain crosslinking techniques, certain crosslinking agents, and/or certain degrees of crosslinking can destroy the remodelable properties of a remodelable material, where preservation of remodelable properties is desired, any crosslinking of the remodelable ECM material can be performed to an extent or in a fashion that allows the material to retain at least a portion of its remodelable properties. Chemical crosslinkers that may be used include for example aldehydes such as glutaraldehydes, diimides such as carbodiimides, e.g., 1-ethyl-3-(3-dimethylaminopropyl)carbodiimide hydrochloride, ribose or other sugars, acyl-azide, sulfo-N-hydroxysuccinamide, or polyepoxide compounds, including for example polyglycidyl ethers such as ethyleneglycol diglycidyl ether, available under the trade name DENACOL EX810 from Nagese Chemical Co., Osaka, Japan, and glycerol polyglycerol ether available under the trade name DENACOL EX 313 also from Nagese Chemical Co. Typically, when used, polyglycerol ethers or other polyepoxide compounds will have from 2 to about 10 epoxide groups per molecule.

Turning now to a discussion of drying techniques that can be useful in certain embodiments of the invention, drying by evaporation, or air drying, generally comprises drying a partially or completely hydrated remodelable material by allowing the hydrant to evaporate from the material. Evaporative cooling can be enhanced in a number of ways, such as by placing the material in a vacuum, by blowing air over the material, by increasing the temperature of the material, by applying a blotting material during evaporation, or by any other suitable means or any suitable combination thereof. The amount of void space or open matrix structure within an ECM material that has been dried by evaporation is typically more diminished than, for example, an ECM material dried by lyophilization as described below.

A suitable lyophilization process can include providing an ECM material that contains a sufficient amount of hydrant such that the voids in the material matrix are filled with the hydrant. The hydrant can comprise any suitable hydrant known in the art, such as purified water or sterile saline, or any suitable combination thereof. Illustratively, the hydrated material can be placed in a freezer until the material and hydrant are substantially in a frozen or solid state. Thereafter, the frozen material and hydrant can be placed in a vacuum chamber and a vacuum initiated. Once at a sufficient vacuum, as is known in the art, the frozen hydrant will sublime from the material, thereby resulting in a dry remodelable material.

In alternative embodiments, a hydrated ECM material can be lyophilized without a separately performed pre-freezing step. In these embodiments, a strong vacuum can be applied to the hydrated material to result in rapid evaporative cooling which freezes the hydrant within the ECM material. Thereafter, the frozen hydrant can sublime from the material thereby drying the ECM material. Desirably, an ECM material that is dried via lyophilization maintains a substantial amount of the void space, or open matrix structure that is characteristic of the harvested ECM material.

Drying by vacuum pressing generally comprises compressing a fully or partially hydrated remodelable material while the material is subject to a vacuum. One suitable method of vacuum pressing comprises placing a remodelable material in a vacuum chamber having collapsible walls. As the vacuum is established, the walls collapse onto and compress the material until it is dry. Similar to evaporative drying, when a remodelable material is dried in a vacuum press, more of the material's open matrix structure is diminished or reduced than if the material was dried by lyophilization.

In certain aspects, the invention provides plugging devices that include a multilaminate material. Such multilaminate materials can include a plurality of ECM material layers bonded together, a plurality of non-ECM materials bonded together, or a combination of one or more ECM material layers and one or more non-ECM material layers bonded together. To form a multilaminate ECM material, for example, two or more ECM segments are stacked, or one ECM segment is folded over itself at least one time, and then the layers are fused or bonded together using a bonding technique, such as chemical cross-linking or vacuum pressing during dehydrating conditions. An adhesive, glue or other bonding agent may also be used in achieving a bond between material layers. Suitable bonding agents may include, for example, collagen gels or pastes, gelatin, or other agents including reactive monomers or polymers, for example cyanoacrylate adhesives. As well, bonding can be achieved or facilitated between ECM material layers using chemical cross-linking agents such as those described above. A combination of one or more of these with dehydration-induced bonding may also be used to bond ECM material layers to one another.

A variety of dehydration-induced bonding methods can be used to fuse together portions of an ECM material. In one preferred embodiment, multiple layers of ECM material are compressed under dehydrating conditions. In this context, the term "dehydrating conditions" is defined to include any mechanical or environmental condition which promotes or induces the removal of water from the ECM material. To promote dehydration of the compressed ECM material, at least one of the two surfaces compressing the matrix structure can be water permeable. Dehydration of the ECM material can optionally be further enhanced by applying blotting material, heating the matrix structure or blowing air, or other inert gas, across the exterior of the compressed surfaces. One particularly useful method of dehydration bonding ECM materials is lyophilization.

Another method of dehydration bonding comprises pulling a vacuum on the device while simultaneously employing the vacuum to press the device together. Again, this method is known as vacuum pressing. During vacuum pressing, dehydration of the ECM materials in forced contact with one another effectively bonds the materials to one another, even in the absence of other agents for achieving a bond, although such agents can be used while also taking advantage at least in part of the dehydration-induced bonding. With sufficient compression and dehydration, the ECM materials can be caused to form a generally unitary ECM structure.

It is advantageous in some aspects of the invention to perform drying and other operations under relatively mild temperature exposure conditions that minimize deleterious effects upon any ECM materials being used, for example native collagen structures and potentially bioactive substances present. Thus, drying operations conducted with no or substantially no duration of exposure to temperatures above human body temperature or slightly higher, say, no higher than about 38° C., will preferably be used in some forms of the present invention. These include, for example, vacuum pressing operations at less than about 38° C., forced air drying at less than about 38° C., or either of these processes with no active heating—at about room temperature (about 25° C.) or with cooling. Relatively low temperature conditions also, of course, include lyophilization conditions.

As well, plugging devices of the invention may be comprised of biocompatible materials derived from a number of biological polymers, which can be naturally occurring or the product of in vitro fermentation, recombinant genetic engineering, and the like. Purified biological polymers can be appropriately formed into a substrate by techniques such as weaving, knitting, casting, molding, and extrusion. Suitable biological polymers include, without limitation, collagen, elastin, keratin, gelatin, polyamino acids, polysaccharides (e.g., cellulose and starch) and copolymers thereof.

Plugging devices of the invention can also include a variety of synthetic polymeric materials including but not limited to bioresorbable and/or non-bioresorbable plastics. Bioresorbable, or bioabsorbable polymers that may be used include, but are not limited to, poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D, L-lactic acid), poly(glycolic acid-co-trimethylene carbonate), polyhydroxyalkanaates, polyphosphoester, polyphosphoester urethane, poly(amino acids), cyanoacrylates, poly(trimethylene carbonate), poly(iminocarbonate), copoly(ether-esters) (e.g., PEO/PLA), polyalkylene oxalates, and polyphosphazenes. These or other bioresorbable materials may be used, for example, where only a temporary blocking or closure function is desired, and/or in combination with non-bioresorbable materials where only a temporary participation by the bioresorable material is desired.

Non-bioresorbable, or biostable polymers that may be used include, but are not limited to, polytetrafluoroethylene (PTFE) (including expanded PTFE), polyethylene terephthalate (PET), polyurethanes, silicones, and polyesters and other polymers such as, but not limited to, polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins, polycarbonates; polyoxymethylenes; polyimides; polyethers; epoxy resins, polyurethanes; rayon; and rayon-triacetate.

Plug bodies useful in the invention can have a variety of shapes. In some forms, a plug body will include an elongate portion having an essentially constant cross-sectional area along its length. Additionally or alternatively, a plug body may include an elongate portion having a varying cross-sectional area along its length, for example, one that tapers in a linear or curvilinear fashion. In this regard, all or a portion of an elongate plug body may be generally cylindrical, conical or conical-like, or otherwise suitably shaped for use in accordance with the present invention. Although not necessary to broader aspects of the invention, in certain embodiments, a single unitary construct provides an elongate plug body in an inventive device. In other embodiments, two or more individual plug body constructs are connected together or otherwise joined to provide a suitable elongate plug body.

The dimensions of a plug body can vary as well. For instance, while a plug body can have any suitable length for use in treating a fistula in accordance with the present invention, in general, a plug body will have a length of at least about 1 cm, and in many instances at least about 3 cm to about 20 cm (approximately 1 to 8 inches). In some preferred embodiments, a plug body will have a length ranging from about 6 cm to about 15 cm (approximately 2 to 6 inches). Suitable plug body lengths will be recognized by those skilled in the art, and therefore, are encompassed by the present invention. In some instances, the length of a plug body is altered before, during and/or after engraftment in a patient. Illustratively, a plug body having excess length can be provided, and this length can be reduced after the plug body is implanted, for example, a proximal portion of a plug body extending from a fistula opening can be trimmed off after the plug body is placed at the treatment site. Additionally, in instances where an elongate plug body portion is considered to have a diameter, the size of this diameter can vary, and may or may not be constant along the length of this portion. At any point along the length of such a plug body portion, the diameter can range from about 0.1 mm to about 25 mm, or more typically from about 5 mm to about 15 mm. In certain forms, a generally conical portion is tapered along its length so that one end of the portion has a diameter of about 5 mm to about 15 mm, while the opposite end of the portion has a diameter of about 0.5 mm to about 5 mm. Such a taper may or may not be continuous along the length of the portion, and may have linear and/or curvilinear characteristics.

The plug members described herein can be formed in a variety of manners including some that involve extrusion, using a mold or form, construction around a mandrel, and/or combinations or variations thereof. In some embodiments, a plug member is formed with a reconstituted or otherwise reassembled ECM material. Plug members can also be formed by folding or rolling, or otherwise overlaying one or more portions of a biocompatible material, such as a biocompatible sheet material. The overlaid biocompatible sheet material can be compressed and dried or otherwise bonded into a volumetric shape such that a substantially unitary construct is formed. In some forms, an inventive device component is constructed by randomly or regularly packing one or more pieces of single or multilayer ECM sheet material within a mold and thereafter processing the packed material. Plug member bodies useful in the invention can be prepared, for example, as described in International Patent Application Serial No. PCT/US2006/16748, filed Apr. 29, 2006, and entitled "VOLUMETRIC GRAFTS FOR TREATMENT OF FISTULAE AND RELATED METHODS AND SYSTEMS" (Cook Biotech Incorporated), which is hereby incorporated by reference in its entirety.

Methods for forming device components useful in the invention can involve manipulating a material within a mold or form. It should be noted that this material may or may not be hydrated when placed in, on, around, etc. the mold or form. In some methods, a substantially dry ECM material (e.g., a powder or sheet material) can be placed in a mold and then suitably hydrated for further processing. In other methods, a hydrated starting material is placed in and/or on a mold or forming structure for further processing. For example, one or more hydrated sheets of ECM material can be applied to a form, e.g., wrapped at least partially around a mandrel so that portions of the sheet(s) overlap. Then, the one or more sheets can be dried, and in some embodiments, dried while under compression, to form a unitary graft construct.

In some modes of operation, a hydrated graft material is provided within a single- or multiple-part mold having a plurality of apertures or holes extending through a wall of the mold, thereby providing access to the mold interior from an external location. These apertures can serve to enhance drying of a hydrated material during a processing step and in processes exerting vacuum pressure at these apertures, can promote and/or facilitate formation of surface protuberances on the graft material as portions of the same are drawn toward the apertures while under vacuum. In one aspect, an amount of ECM material is retained in such a mold, and needles or other material-displacing objects are inserted through some or all of the mold apertures and a distance into the ECM material, thereby displacing volumes of the ECM material. This can be performed when the graft material is hydrated, partially hydrated or dehydrated. In some forms, with needles inserted in a hydrated ECM material and providing passages therein, the material is subjected to conditions (e.g., freezing and/or dehydrating conditions) which, alone or in combination with one or more other conditions, cause or allow the passages to be generally retained in the ECM material after the needles are removed.

In one embodiment, one or more sheets of hydrated ECM material are suitably wrapped and/or randomly packed around a mandrel, and then a mold having a plurality of holes extending through a wall of the mold is placed around the material-covered mandrel, for example, so that an amount of pressure is placed on the ECM material. The mandrel can then optionally be removed. Thereafter, needles or other material-displacing objects are inserted through some or all of the holes and at least partially through the ECM material, thereby displacing volumes of the ECM material. The ECM material is then at least partially dried. In some aspects, a suitable lyophilization technique is employed, e.g., one with or without a pre-freezing step as described herein. In these or other drying methods in which needles or other penetrating elements are to be left within the mass during drying, these elements can optionally be provided with a plurality of apertures or holes or can otherwise be sufficiently porous to facilitate the drying operation by allowing the passage of hydrate from the wet mass. In one embodiment, a hydrated ECM material with emplaced needles can be subjected to freezing conditions so that the material and any contained hydrate become substantially frozen. Thereafter, the needles can be removed from the ECM material, and the remaining construct (with the frozen material passages substantially retaining their shape) can be placed under a vacuum so that the frozen hydrant sublimes from the material, thereby resulting in a dry graft construct with retained passages therein.

In other modes of operation, passage-forming structures can be incorporated integrally into a mold so that passageways are formed upon introducing the starting material in and/or on the mold. In these aspects, the passage-forming structures can be part of the mold (e.g., extend from a surface of the mold), or they can be separate objects attached or otherwise coupled to the mold, to provide the desired passage or passages through the ultimately-formed graft body.

Although not necessary to broader aspects of the invention, in some aspects, the formation of such a graft construct comprises wrapping one or more sheets of hydrated graft material around a mandrel a number of times. The resulting roll of graft material is then introduced into a mold, and the mandrel is removed (optional), e.g., before or after applying the mold. Thereafter, multiple material-displacing objects such as but not limited to needles are forced through apertures in the mold and into the hydrated graft material, and the material is subjected to one or more drying techniques such as a lyophilization process. In other aspects, the formation of such a graft construct includes placing a flowable graft material into a mold and then subjecting the graft material to further processing. For example, a flowable ECM material mass, such as a gel, paste or putty, potentially incorporating a particulate ECM material, can be placed into a mold, and then with volumes of material displaced in the mass (e.g., by penetrating needles), the ECM material can be dried or otherwise caused to form an integral piece to provide a graft body having passages therein. Illustratively, each of the passages can be provided by forcing a single object through the material mass, or alternatively, where a mandrel is left in place to form a longitudinal lumen, by forcing two objects into the mass and toward one another from opposite directions until they abut the mandrel. The mass can then be processed to a solid graft body as discussed herein.

In one aspect, a plug member to be positioned in bodily passage or other similar opening comprises a compliant, biocompatible sheet-form material, for example, one or more layers of ECM material that can be forced into a fistula tract. Such sheet-form plug members can be prepared, for example, as described in International Patent Application Serial No. PCT/US2006/16233, filed Apr. 29, 2006, and entitled "FISTULA GRAFT WITH DEFORMABLE SHEET-FORM MATERIAL" (Cook Biotech Incorporated), which is hereby incorporated by reference in its entirety.

Inventive devices may be used to plug or otherwise fill a variety of passages and other open spaces in the body. In some instances, these open spaces will occur naturally in the body, for example, as a native lumen or other open space in a bodily system, e.g., in an organ or other component of the circulatory, respiratory, digestive, urinary and reproductive, sensory, or endocrine systems. In certain aspects, a space to be filled is one that exists naturally in the body but relates to a disease, defect, deformation, etc. Alternatively, an opening or passage to be filled may be one resulting from an intentional or unintentional trauma to the body including but not limited to some relating to vehicular accidents, gunshots and other similar wounds, etc., as well as some formed by passage of a medical instrument (e.g., a needle, trocar, etc.) through cutaneous, subcutaneous, and/or intracutaneous tissue.

Illustratively, inventive devices, alone or in conjunction with one or more other suitable objects, can be used to occlude, or at least promote and/or facilitate occlusion of, a lumen or other open space in the vasculature, e.g., a blood vessel such as a vein or artery, or a lumen or open space of a fallopian tube, e.g. in a procedure to provide sterility to a female patient. In certain aspects, one or more devices of the invention are deployed within the venous system (e.g., within the greater and/or lesser saphenous vein) to treat complications, such as a varicose vein conditions. In other embodiments, inventive devices are used as contraceptive devices. In some preferred aspects, inventive devices are used to treat fistulae including but not limited to urethro-vaginal fistulae, vesico-vaginal fistulae, tracheo-esophageal fistulae, enterocutaneous fistulae including gastro-cutaneous fistulae, and any number of anorectal fistulae, such as recto-vaginal fistula, recto-vesical fistulae, recto-urethral fistulae, or recto-prostatic fistulae.

In certain embodiments, a plugging device includes an element that can serve as an imageable position marker, for instance susceptible to visualization using x-ray, magnetic resonance imaging, ultrasonic, or other imaging techniques. Beneficially, the imageable position marker can be a radiopaque element. For example, a device component such as capping member 59 can be made of or comprise a radiopaque substance. A radiopaque substance can be incorporated in any suitable manner, including but not limited to inclusion as a radiopaque coating, an attached radiopaque object, or an integrated radiopaque substance. In certain forms, capping member 59 and/or another device component can be formed of a biocompatible polymeric material loaded with a particulate radiopaque material. Suitable radiopaque substances include but are not limited to tantalum, such as tantalum powder, gold, bismuth, iodine, and barium, as well as other suitable known materials capable of detection under x-ray imaging techniques.

Turning now to a more detailed description of delivery devices useful in the invention, these devices can exhibit a variety of shapes and sizes, and may be formed with one or more of a variety of materials. Whether naturally derived or non-naturally derived, a particular material may be selected to take advantage of one or more properties of the material such as but not limited to its weight, durability, flexibility, etc. For example, a device may be formed with a material that is somewhat flexible but otherwise has properties enabling the device to traverse a body passageway without buckling or kinking. And in this regard, a delivery device, or any portion thereof, may be rigid, malleable, semi-flexible, or flexible.

In some aspects, a delivery device is rigid or substantially rigid, and is configured to be generally straight, for example, for use in treating certain simple or straight fistulae. Alternatively, delivery devices useful in the invention can be configured to include one or more portions that are curvilinear, bent, or otherwise suitably shaped. In certain aspects, the distal end of a delivery device is curved to a degree to allow for easier passage of the distal end through a complex fistula, e.g., a horseshoe fistula. In some forms, a delivery device is composed of a malleable material such as but not limited to a woven or spirally-configured metal or alloy material, or a plastic (hydrocarbon-based) material, which may be bent to the necessary angle or curvature, for example, to allow passage through a fistula tract. The shape of such a delivery device may be adjusted at certain intervals of the procedure so as to allow the delivery device to pass further and further into the fistula tract, until the primary opening is identified. In some forms, the delivery device is generally straight in a relaxed condition but can flex to adapt to contours during passage.

In some of these embodiments, the device is configured to be directable or steerable through the passageway, and therefore, exhibits desirable characteristics, e.g., sufficient stiffness, to allow an operator to apply an adequate degree of ante-grade force to the device to allow it to traverse a passageway in a desirable manner. In one aspect, a delivery member such as delivery member 31 is configured to have varying properties (e.g., flexibility) along its length. Illustratively, delivery member 31 may be rigid near handle 30 and somewhat flexible in other locations, for example, in more distal regions of the member. In some forms, a delivery device will be somewhat rigid in terms of column strength, yet will be equipped with one or more reliefs, indentations, thinner portions, or other similar adaptations along the device to provide some lateral flexibility to the device. Additionally or alternatively, a device may incorporate a mechanism of some sort that enables an operator to steer or otherwise navigate the device through a tortuous body passageway. These and other adaptations for facilitating advancement of a device through a body passageway will be recognized by those skilled in the art, and therefore, are encompassed by the present invention.

Suitable materials for forming a delivery device useful in the invention include but are not limited to metallic materials including stainless steel, titanium, cobalt, tantalum, gold, platinum, nickel, iron, copper and the like, as well as alloys of these metals (e.g., cobalt alloys, such as Elgiloy®, a cobalt-chromium-nickel alloy, MP35N, a nickel-cobalt-chromium-molybdenum alloy, and Nitinol®, a nickel-titanium alloy). Additionally or alternatively, a delivery device can include material in the form of yarns, fibers, and/or resins, e.g., monofilament yarns, high tenacity polyester, and the like. A delivery device can also include other plastic, resin, polymer, woven, and fabric surgical materials, other conventional synthetic surgical materials, such as a shape-memory plastic, and/or combinations of such materials. Further, appropriate ceramics can be used, including, without limitation, hydroxyapatite, alumina and pyrolytic carbon.

In certain embodiments, a delivery device will be used to deliver a plug body into a fistula tract. Such a device may have a length of about 2 inches to about 12 inches, more typically about 3 inches to about 9 inches, and even more typically about 4 to about 8 inches. Also, these devices may have an outside diameter of about 0.3 mm to about 3.2 mm, more typically about 0.5 to about 3.0 mm, and even more typically about 1.0 mm to about 2.5 mm.

Referring now to FIGS. 2A through 2C, shown is another fistula plug delivery apparatus 50 of the present invention. Apparatus 50 includes a fistula plug 51 and a removable delivery device 52. Fistula plug 51 is comprised of a plug body 55 having a distal portion 56 and a proximal portion 57. Plug body 55 exhibits a generally cylindrical shape, and has a central lumen 58 extending therethrough along its length. In some preferred aspects, plug body 55 is comprised of a collagenous material, although it may be formed with one or more of a variety of materials as discussed more elsewhere herein.

An optional disc-shaped capping member 59 is attached to plug body distal portion 56, e.g., with an adhesive or by any other suitable attachment means. Capping member 59, which has roughly the same diameter as plug body 55, has a center hole occurring therein. Capping members useful in the invention such as member 59 can be any suitable size and shape, and may be formed with one or more of a variety of materials. Delivery device 52 includes an elongate delivery member 60. A handle 61 is attached to the proximal end of the delivery member. Delivery member 60 is sized and configured to be passed through plug body lumen 58, as well as through the hole in capping member 59, and in this regard, can extend entirely through plug body 55 and capping member 59 as shown in FIG. 2C.

Delivery apparatus 50 further includes an optional introducer member 64. When used in the invention, introducer members can exhibit a variety of shapes and sizes, and may be formed with one or more of a variety of materials. In some forms, an introducer member includes a radiopaque element. Introducer member 64 has a proximal portion 65 and a distal portion 66 that includes a rounded, "leading" tip. Introducer member 64 also has a central lumen 68 extending partially therethrough along its length. A portion of introducer member 64 is tapered from proximal portion 65 toward distal portion 66 to provide a generally conical shape. While an introducer member need not be attached to any other portion of a delivery apparatus, in the current embodiment, the proximal portion 65 of introducer member 64 is attached to capping member 59 with an absorbable coupling element such as an adhesive, 2-0 vicryl suture material, etc.

Delivery member 60 is sized and configured to be passed into introducer member lumen 68. Thereafter, it can be advanced until its distal end contacts the introducer member wall defining this lumen terminus. Such contact can provide a counterforce when pushing the introducer member through a body passageway with delivery device 52. In the current embodiment, delivery member 60 does not attach to introducer member 64. In other embodiments, a delivery member such as member 60 is configured to attach to or otherwise be united with one or more other apparatus components. Illustratively, a distal portion of an elongate delivery member can be attached to an introducer member and/or any other apparatus component in such a way that the operator can detach the delivery member from the other component(s) during a delivery step.

In alternative embodiments, the invention provides apparatuses similar to apparatus 50 except not including an introducer member. These apparatuses may be adapted in any suitable manner to enable a fistula plug such as plug 51 to be forced into a fistula tract with a delivery device such as device 52. Illustratively, plug body 55 may instead be configured similarly to the plug body shown in FIG. 1. Additionally or alternatively, a capping member similar to capping member 59 may be utilized, wherein the capping member does not have a center hole that allows the delivery member to pass therethrough. In some embodiments, a delivery member such as member 60 is releasably attached to a plug body such as plug body 55 and/or, if present, a capping member such as capping member 59. These and other adaptations for enabling delivery of a fistula plug with an inventive apparatus that does not include an introducer member will be recognized by the skilled artisan and are encompassed by the present invention.

Delivery apparatus 50 also includes an optional protective sleeve 70 positioned around plug body 55. Protective sleeves useful in the invention such as sleeve 70 can be sized and adapted in a variety of fashions, and can be formed with one or more of a variety of materials, for example, synthetic polymeric materials such as but not limited to ePTFE. A protective sleeve may be useful, in some forms, to shield or otherwise protect a fistula plug before, during and/or after its delivery into a fistula tract, for example, to shield a plug from hydrate at the implantation site when such shielding is desired. Protective sleeve 70, which is generally in the form of a thin-walled, hollow tube, has a distal portion 72 and a proximal portion 73. In the current embodiment, sleeve 70 is attached to introducer member 64 with an adhesive, although other modes of bonding or coupling the two components together are contemplated as within the scope of the present invention.

Sleeve 70 includes grasping portions 80, and has a longitudinal tear-line 75 occurring therein, which are both configured to facilitate removal of sleeve 70 from the fistula tract in a delivery step as discussed more thoroughly below. These and other adaptations for facilitating removal of sleeve 70 will be recognized by those skilled in the art, and therefore, are encompassed by the present invention. Nonetheless, it will be understood that protective sleeves useful in the invention such as sleeve 70 need not be removed from the fistula tract at all. In some embodiments, a protective sleeve is suitably adapted so that all or a portion of the sleeve can remain in the fistula tract indefinitely or for a certain period of time following implantation. Such a protective sleeve may, in some aspects, be formed with a suitable resorbable material, and in a preferred aspect, is comprised of a remodelable material.

As shown in FIG. 2B, sleeve 70 is positioned on introducer member 64 so that the edge of distal portion 72 is located just beyond the region where capping member 59 and introducer member proximal portion 65 meet, thus covering this region. A horizontal tear-line 77 occurs just proximally of this region. Tear-line 77 is configured to facilitate removal of sleeve 70 in a delivery step as discussed more thoroughly below. Although not necessary to broader aspects of the invention, in embodiments that do not include an introducer member, sleeve 70 may instead be bonded, coupled or otherwise attached to another apparatus component (e.g., a fistula plug, capping member and/or delivery member). These and other adaptations for incorporating a protective sleeve into a delivery apparatus when an introducer member is not present will be recognized by the skilled artisan, and therefore, are encompassed by the present invention. In some forms, regardless of whether an introducer member is present, a protective sleeve is not attached to any other part of the delivery apparatus, yet is positioned around the apparatus, or a portion thereof, and is able to remain generally in this position during delivery through a fistula tract.

Delivery apparatus 50 can be used in a variety of manners to deliver fistula plug 51 into a fistula tract. Illustratively, an operator can grip handle 61, and insert the distal tip of introducer member 64 into a fistula tract through a secondary fistula opening. Thereafter, delivery device 52 can be further advanced through the tract toward a primary fistula opening, wherein plug body 55 is forced through the tract by delivery device 52, e.g., by the distal end of delivery member 60 contacting a portion of the introducer member adjacent to the distal terminus of lumen 68. Delivery device 52 can be advanced until at least a portion of introducer member 64 passes through the primary opening and into the alimentary canal, for example, until capping member 59 is positioned at or near the primary opening. Thereafter, the operator can grasp grasping portions 80 and start to tear sleeve 70 along longitudinal tear-line 75 and toward its distal end, thereby exposing plug body proximal portion 57, which may be located at the secondary opening or extending a distance into or out from the secondary opening. While holding plug body 55 and delivery device 52 in place in the tract, the operator can then sufficiently pull on sleeve 70 until it fully separates along horizontal tear-line 77. This more proximal portion of sleeve 70 can then be removed from the tract and discarded. Delivery device 52 can be further advanced at this point if desired.

Tear-line 75 is essentially a plurality of small, spaced-apart slits that form a line along the length of sleeve 70. Other suitable adaptations for facilitating removal of sleeve 70 from the body will be recognized by the skilled artisan, and therefore, are encompassed by the present invention. Illustratively, a protective sleeve can incorporate scores, thinner portions, and other openings and non-openings that weaken a portion of the sleeve to facilitate a tear-away operation in removing the sleeve from the tract. Such a weakened portion may include any suitable means for facilitating tearing or breaking along the area. In certain beneficial forms, a protective sleeve such as sleeve 70 is controllably separable longitudinally into two or more pieces for removal, for example, as occurs in Peel-Away® catheters available from Cook Incorporated, Bloomington, Ind., USA. Such an apparatus with a separable sleeve is particularly useful in treating fistulae that have a secondary opening in the outer skin surface and a primary opening that is relatively difficult to access other than through the fistula tract, e.g. as occurs in a large percentage of enterocutaneous fistulae.

While still holding plug body 55 in place in the tract, the delivery device 52 can be withdrawn back through the fistula tract, and thus, removed from plug body 55 and any other apparatus components remaining in the tract. In some cases, it may be desirable to adjust or otherwise manipulate plug body 55 during a delivery step, for example, by hydrating the plug, trimming off portions of the plug extending from the secondary opening (if applicable), securing (e.g., suturing) the plug to portions of the patient's skin adjacent to secondary opening, etc. Sometime following implantation, introducer member 64 can then uncouple or otherwise disengage from capping member 59 (at least due in part to degradation of the absorbable element coupling them together), allowing introducer member 64 to be discarded, e.g., to pass through and out of the bowel with naturally occurring fecal mater. In some instances, such decoupling can be facilitated and/or promoted by naturally occurring forces generated during peristalsis.

In other embodiments, introducer member 64 is not attached to capping member 59 (or is attached to capping member 59 and/or another apparatus component in such a manner that enables the operator to detach introducer member 64 from the remainder of the apparatus during a delivery step). In these embodiments, delivery device 52 can be advanced through the fistula tract until introducer member 64 passes through the primary opening and falls away into the alimentary canal on its own or following sufficient manipulation by the operator, leaving capping member 59 positioned at or near the primary opening. Alternatively, an introducer member 64 that is attached to one or more other apparatus components can be configured to remain attached thereto, for example, to reside in and/or around the primary opening to block the primary opening following implantation. Such an introducer member may, in some aspects, be formed with a suitable resorbable material, and in a preferred aspect, is comprised of a remodelable material.

Delivery member 60 is not attached to any other apparatus component in the current embodiment. In other embodiments, a distal portion of delivery member 60 is attached to one or more other apparatus components (e.g., introducer member 64 and/or plug body 55) in such a fashion that enables the operator to detach delivery member 60 therefrom during a delivery step. Illustratively, delivery member 60 can be bonded to introducer member 64 so that the two remain bonded when advancing the plug through the tract, but detach from one another when member 64 is sufficiently pulled, twisted, jerked, etc., while holding plug body 55 in place in the tract. In some modes of operation, an introducer member is not equipped with a central lumen, and a delivery member is coupled to the introducer member with an adhesive, using a lightweight weld, etc.

Capping members such as capping member 59, when utilized in present invention, can exhibit a variety of shapes, sizes and configurations. In general, a fistula graft including a capping member will be configured to have portions residing in and around a fistula opening, e.g., a primary fistula opening. For example, some fistula grafts useful in the invention include a biocompatible graft body which is configured to block at least the primary fistula opening, wherein the graft body includes a capping member and an elongate plug body, which extends from the capping member. The capping member is configured to contact portions of the alimentary canal wall adjacent to the primary opening, and the plug body is configured to extend into at least a portion of the fistula tract. A capping member and an elongate plug member may be formed separately and then attached to one another or otherwise suitably united, or alternatively, the two may be formed as a single unit, for example, from a single piece of material or other object. When formed separately, the two members may be united, for example, using an adhesive, by suturing, using mechanical fastener(s), and/or employing any other suitable joining means. Each of the two members may be formed with one or more of a variety of suitable biocompatible materials.

A capping member can include one or more objects (e.g., devices, pieces of material, etc.) that, together or alone, exhibit a three-dimensional rectilinear or curvilinear shape. Suitable three-dimensional rectilinear shapes can have any suitable number of sides, and can include, for example, cubes, cuboids, tetrahedrons, prisms, pyramids, wedges, and variations thereof. Suitable three-dimensional curvilinear bodies can include, for example, spheres, spheroids, ellipsoids, cylinders, cones, and any suitable variations thereof (e.g., a segment of a sphere, or a truncated cone, etc.). Capping members and capped plugs useful in the invention can be prepared, for example, as described in International Patent Application Serial No. PCT/US2006/024260, filed Jun. 21, 2006, and entitled "IMPLANTABLE GRAFT TO CLOSE A FISTULA" (Cook Biotech Incorporated); and U.S. Provisional Patent Application Ser. No. 60/763,521, filed Jan. 31, 2006, and entitled "FISTULA GRAFTS AND RELATED METHODS AND SYSTEMS FOR TREATING FISTULAE" (Cook Biotech Incorporated), which are hereby incorporated by reference in their entirety. In some aspects, a fistula plug includes more than one capping member, for example, a capping member to be positioned at a primary fistula opening and a capping member to be positioned at a secondary fistula opening. In preferred aspects, a capping member and/or a plug body comprise a remodelable, angiogenic material, for example, a remodelable extracellular matrix material such as submucosa.

In embodiments where a plug body and a capping member are formed as separate constructs, the two may be coupled to one another with an absorbable coupling device or material. These coupling elements can exhibit any suitable size, shape, and configuration, and in some aspects, take the form of an adhesive or one or more hooks, fasteners, barbs, straps, suture strands, or combinations thereof. Also, such coupling elements may be comprised of one or more of a variety of suitable biocompatible materials exhibiting a rate of degradation upon implantation in vivo, such as but not limited to a 2-0 vicryl suture material. Illustratively, a coupling element can be adapted to desirably hold a capping member and plug body in association with another during product handling and implantation, and then upon implantation, to degrade at a desirable rate. In some modes of operation, the capping member and plug body, at least due in part to degradation of the coupling element, can uncouple or otherwise disengage from one another after a period of time following implantation, allowing the capping member to be discarded, e.g., to pass through and out of the bowel with naturally occurring fecal mater. In some instances, such decoupling can be facilitated and/or promoted by naturally occurring forces generated during peristalsis.

A capping member, in certain aspects, comprises an expandable element, for example, an expandable material such as a compressed sponge material and/or an expandable device such as a resilient wire frame. An expandable capping member useful in the invention can be adapted to self-expand, for example, upon removal from a chamber or other space in a delivery device, or alternatively, when a device being used to constrain the capping member (e.g., a suture) is removed or otherwise manipulated. In one embodiment, the capping member 59 includes a frame comprising a single piece of superelastic wire or other suitable material having a plurality of sides and bends interconnecting adjacent sides. The bends can be coils, fillets, or other configurations to reduce stress and fatigue. The single piece of wire is preferably joined by an attachment mechanism, such as a piece of cannula and solder, to form a closed circumference frame. In some aspects, a capping member is configured to expand upon sufficient manipulation by an operator (e.g., by pushing or pulling a cord or other expansion component when expansion is desired).

Such a capping member frame can comprise a metallic material including but not limited to stainless steel, titanium, cobalt, tantalum, gold, platinum, nickel, iron, copper and the like, as well as alloys of these metals (e.g., cobalt alloys, such as Elgiloy®, a cobalt-chromium-nickel alloy, MP35N, a nickel-cobalt-chromium-molybdenum alloy, and Nitinol®, a nickel-titanium alloy). Additionally or alternatively, suitable frames can include material in the form of yarns, fibers, and/or resins, e.g., monofilament yarns, high tenacity polyester, and the like. A frame element can also include other plastic, resin, polymer, woven, and fabric surgical materials, other conventional synthetic surgical materials, such as a shape-memory plastic, and/or combinations of such materials. Further, appropriate ceramics can be used, including, without limitation, hydroxyapatite, alumina and pyrolytic carbon. Such metallic and other materials may be used in forming other expandable and non-expandable fistula graft components useful in the present invention. Capping member 59 also includes a flexible material covering extending between sides of the frame. Such a covering can be formed with any suitable material such as but not limited to DACRON, PTFE, collagen, submucosa, and other flexible materials, and can be attached to the frame with sutures or other suitable attachment means.

Figure 3A:
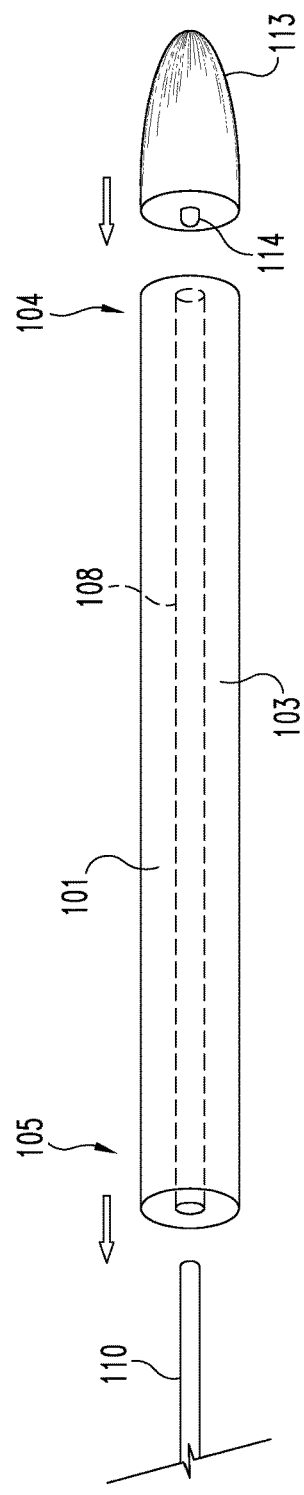
FIG. 3A provides an exploded perspective view of another fistula plug delivery apparatus according to the present invention.
Figure 3B:
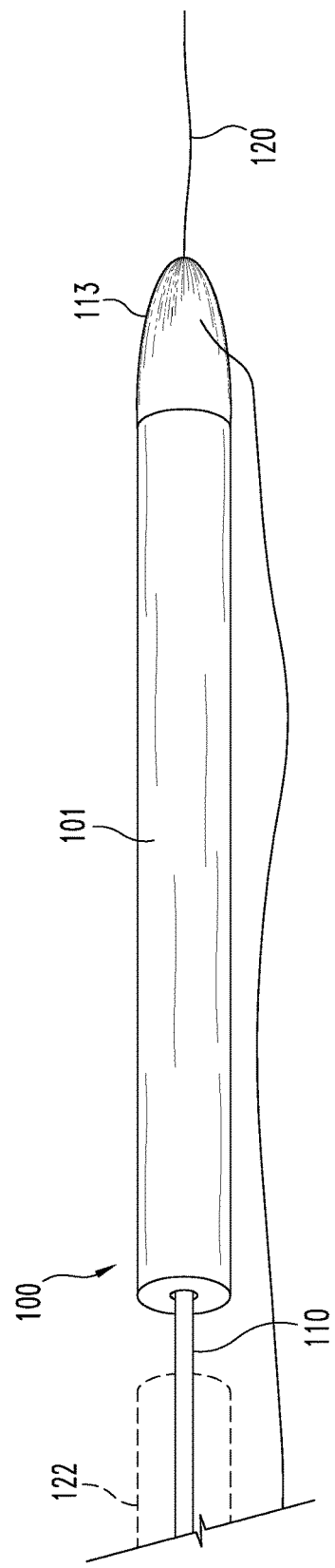
FIG. 3B is a perspective view of the fistula plug delivery apparatus of FIG. 3A.

FIGS. 3A and 3B illustrate yet another fistula plug delivery apparatus 100 of the present invention. Apparatus 100 includes a fistula plug 101, which is comprised of a plug body 103 having a distal portion 104 and a proximal portion 105. Plug body 103 exhibits a generally cylindrical shape, and has a central lumen 108 extending therethrough along its length. Apparatus 100 also includes an elongate delivery member 110, and an introducer member 113 having a nipple 114 extending from its proximal end as shown. Delivery member 110 has a lumen communicating with a distal end opening. Nipple 114 is configured to snugly fit in this lumen. In one embodiment, this lumen extends through a substantial portion of delivery member 110. Although not necessary to broader aspects of the invention, in the current embodiment, introducer member 113 has a channel therein through which a guidewire 120 can be received.

Delivery member 110 is sized and configured for passage through plug body lumen 108 and over nipple 114, and in this regard, the various device components may be assembled in the direction of the arrows shown in FIG. 3A. Once the device is assembled, its components may or may not be joined to one another. Illustratively, introducer member 113 may be attached to plug body 103, delivery member 110, or both. Thus, while friction may be enough to suitably hold delivery member 110 in contact with nipple 114, in some embodiments, the delivery member will be releasably attached to the introducer member for delivery, and then the two will be detached in a later step. In an alternative embodiment, introducer member 113 will be equipped with a central lumen similar to that of the introducer member shown in FIG. 2C for receiving a delivery member.

When assembled as shown in FIG. 3B, delivery member 110 can be used to push introducer member 113 through a body passageway along guidewire 120. Thus, in embodiments where introducer member 113 and plug body 103 are suitably joined, delivery member 110 can also be used to advance fistula plug 101 through the passageway. Additionally or alternatively, an optional pusher device 122 may be received over delivery member 110. Such a device can be configured to translate freely along delivery member 110, and in this regard, may be used to push fistula plug 101 and the associated introducer member 113 along guidewire 120.

These and some other apparatuses of the invention are particularly useful in treating gastro-cutaneous, entero-cutaneous, colo-cutaneous and other blind-ending fistulae, for example, wherein the distal end of a wire guide such as wire 120 can be advanced through a fistula tract from a secondary fistula opening in the skin and toward a primary fistula opening at a subcutaneous location in the body. In some instances, it may be desirable to employ a wire guide that is configured to be directable or steerable through the fistula tract or other body passageway. Examples of such devices can be found, for example, in pending U.S. application Ser. No. 11/234,990, filed Sep. 26, 2005, and entitled "STEERABLE LOOP TOP WIRE-GUIDE."

In one mode of operation, the distal end of guidewire 120 is passed into an enterocutaneous fistula tract through a secondary fistula opening and toward a primary fistula opening, potentially under fluoroscopic guidance. The wire is advanced until its distal end enters the alimentary canal through the primary opening. With guidewire 120 extending entirely through the tract, apparatus 100 is associated with the wire by passing the proximal end of the wire through the channel in introducer member 113.

The distal tip of introducer member 113 is then positioned at the secondary opening, and apparatus 100 is forced into the fistula tract through the secondary opening. This can be accomplished in any suitable manner, for example, by techniques that involve holding pusher device 122 in direct contact with plug body proximal portion 105, and moving delivery member 110 and pusher device 122 in unison to deliver the plug into the tract. Thereafter, apparatus 100 can be further advanced through the tract toward a primary fistula opening, wherein plug body 103 is forced through the tract by pusher device 122. Apparatus 100 can be advanced until at least a portion of introducer member 113 passes through the primary opening and into the alimentary canal, for example, until a very slight segment of plug body distal portion 104 extends into the alimentary canal. Again, positioning of the plug members can be aided by fluoroscopic imaging. At this point, plug body proximal portion 105 will be located at the secondary opening or extending a distance into or out from the secondary opening. Together or separately, guidewire 120 and delivery member 110 can be withdrawn back through the fistula tract, thus allowing introducer member 113 to fall away into the alimentary canal. When withdrawing these apparatus components from the fistula tract, pusher device 122 can be placed in contact with plug body proximal end 105 to provide back pressure, thus maintaining desirable positioning of the plug body inside the tract.

In some cases, it may be desirable to adjust or otherwise manipulate plug body 103 at some point in the delivery, for example, by trimming off portions of the plug extending from the secondary opening (if applicable) and suturing the plug to portions of the patient's skin adjacent to secondary opening. In some preferred embodiments, care is taken to not block or otherwise close the secondary opening to facilitate drainage of the tract following the implantation procedure, for example, during remodeling when a remodelable material is utilized in the plugging assembly. Alternatively, in embodiments where introducer member 113 is attached to one or more other apparatus components, the introducer member can be configured to remain attached to the components, and to reside at the treatment site following implantation, e.g., in and/or around a primary fistula opening to block the opening.

In certain embodiments, the present invention provides devices that are configured for placement in a body passageway or other opening, and are comprised of a removable, first device component positioned in a second device component. Although not necessary to broader aspects of the invention, in a preferred embodiment, the second component is delivered into the body passageway with the first component positioned in the second component. Once the second component is desirably placed, the removable first component may be removed from the second component, although in some aspects, the first component, or a portion thereof, will be left in the second component indefinitely or for a particular period of time following the initial placement. Some of these devices are fistula plugs for delivery into a fistula tract. In one embodiment, a fistula plug includes an elongate plug body and a removable core material received therein. Such a core material, when positioned in a plug body, can be effective to add column strength to the plug body for enhancing its delivery into a fistula tract.

Figure 4A:
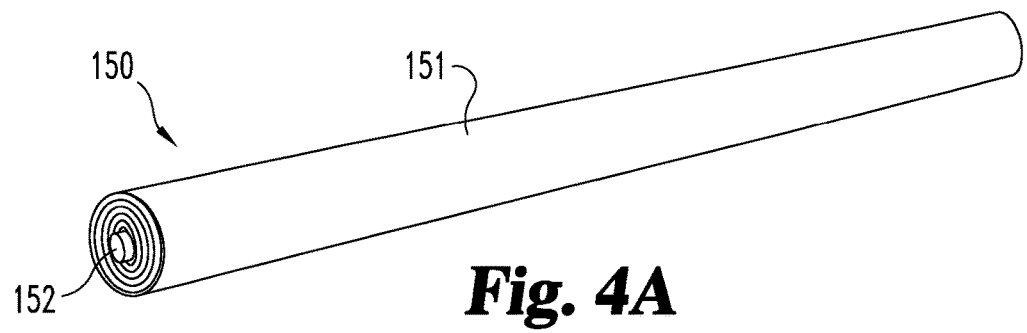
FIG. 4A is a perspective view of a fistula plug according to one embodiment of the present invention.
Figure 4B:
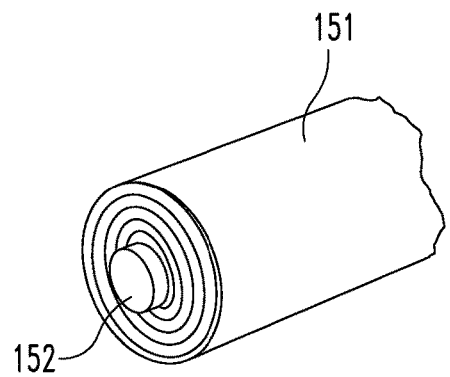
FIG. 4B is an enlarged, partial view of the fistula plug of FIG. 4A.

With reference now to FIG. 4, shown is fistula plug 150 that includes an elongate plug body 151 and a removable core material 152 received in the plug body. When so positioned, core material 152 is effective to increase the column strength of plug body 151. Core material 152 is generally in the shape of a cylinder, and is formed with a synthetic polymeric material, e.g., Nitinol. Plug body 151 is comprised of a rolled sheet-form material (e.g., a naturally-derived material in sheet form), and when positioned around core material 152, gives plug 150 a generally cylindrical shape. In some forms, a plug body such as body 151 is formed with a rolled collagen-containing material, wherein the rolled material layers are compressed and bonded together to as to form a substantially unitary construct.

Plug body 151 and core material 152 may each be formed with one or more of a variety of materials including some that are naturally derived and some that are non-naturally derived. These include materials that are in sheet form and materials that are not in sheet form. Further, while core material 152 is configured to add column strength to plug body 151 when positioned therein, plug body 151 and core material 152 can each be considered to be rigid, malleable, semi-flexible, or flexible when examined separately. In certain aspects, a plug body and a core material are comprised of one or more of the same materials. Illustratively, a plug body such as plug body 151 may be formed with an ECM material such as a remodelable, angiogenic SIS material, while a core material such as core material 152 may be formed with the same material except being physically, chemically and/or otherwise modified to be relatively more rigid than the "pre-modified" material of the plug body. As well, fistula plug 150, and any of its components including plug body 151 and core material 152, can exhibit a variety of shapes and sizes for delivery into a body passageway or other opening, and in some aspects, will include a generally cylindrical portion and/or a generally conical portion.

An inventive plug such as fistula plug 150 can be formed in any suitable manner. Illustratively, a plug body such as plug body 151 can be formed directly around a core material such as core material 152. In some forms, a plug body and a core material are formed separately and then combined. Although not necessary to broader aspects of the invention, in one embodiment, a plug body is formed so as to provide a designated opening (e.g., a lumen or other passage) into which a core material can be removably positioned. Illustratively, a plug body may be formed separately (e.g., around a mandrel similar in diameter to a core material) such that a passage is formed in the plug body. Thereafter, the core material is positioned in this passage. Also, a core material may include one or more individual core material structures. When a multitude of core material structures are utilized in a device, these structures may or may not be connected to one another when positioned in a plug body.

In this particular embodiment, plug body 151 is formed with a single layer of material wrapped around core material 152. In alternative embodiments, plug body is formed with two or more layers of material, wherein a given layer may or may not be the same as another layer. Once wrapped fully around a core material, the outer edge of a material layer can then be fixed to an underlying wrapped layer. Additionally or alternatively, a thin layer of adhesive can be applied to each successive underlying layer as a rolled construct is formed so that a substantial portion of the rolled layers are adhered to one another. Any of these techniques may additionally involve compression and drying steps. Further, a plug body such as plug body 151 may be comprised of a material that is not in layer form. Such "non-layered" material can be formed in any suitable manner including but not limited to by extrusion, using a mold or form, construction around a mandrel, and/or combinations or variations thereof. In some embodiments, such a portion is formed with a reconstituted or otherwise reassembled ECM material.

An inventive device, or any component thereof, can itself be considered lubricious by those skilled in the art. In some forms, a device or one or more device components will include a layer (e.g., a coating) to enhance the lubricious properties of the component(s). Such a layer may be applied (e.g., by spraying, dip coating, over-extruding or by any other suitable means) to the component(s), and may be comprised of a hydrophilic material such as but not limited to parylene or PTFE. In certain aspects, UV (ultra-violet light)-curable, radiation-curable, photoreactive, photoimmobilizing, and other similar coatings are used. These coatings have in common at least one photoreactive species. Coatings can be made from these species, and then all or a portion of a tissue augmentation device can be coated and the coating cured. Lubricous coating materials include those commercially available from SurModics, Inc., Eden Prairie, Minn., under the trade mark "PhotoLink™."

Additionally, an inventive device, or any component thereof, can incorporate an effective amount of one or more antimicrobial agents or therapeutic agents otherwise useful to inhibit the population of the device or surrounding tissue with bacteria or other deleterious microorganisms. Illustrative such agents can include, for example, antibiotics such as penicillin, tetracycline, chloramphenicol, minocycline, doxycycline, vancomycin, bacitracin, kanamycin, neomycin, gentamycin, erythromycin and cephalosporins. Examples of cephalosporins include cephalothin, cephapirin, cefazolin, cephalexin, cephradine, cefadroxil, cefamandole, cefoxitin, cefaclor, cefuroxime, cefonicid, ceforanide, cefotaxime, moxalactam, ceftizoxime, ceftriaxone, and cefoperazone, and antiseptics (substances that prevent or arrest the growth or action of microorganisms, generally in a nonspecific fashion) such as silver sulfadiazine, chlorhexidine, glutaraldehyde, peracetic acid, sodium hypochlorite, phenols, phenolic compounds, iodophor compounds, quaternary ammonium compounds, and chlorine compounds. These or other therapeutic agents can be incorporated directly on or in an inventive device, or they can be incorporated with a suitable binder or carrier material, including for instance hydrogel materials. The carrier or binder coating can be applied to the device by any suitable means including, for example, spraying, dipping, etc. as known in the art. The antimicrobial or other therapeutic agent can be added to the carrier/binder coating either prior to or after application of the coating to the device.

In certain aspects of the invention, treatment of a fistula includes an endoscopic visualization (fistuloscopy) step that is performed prior to implanting a fistula plug. Such endoscopic visualization can be used, for example, to determine the shape and size of a fistula, which in turn can be used to select an appropriately sized and shaped fistula graft device for treating the fistula. Illustratively, a very thin flexible endoscope can be inserted into a secondary opening of the fistula and advanced under direct vision through the fistula tract and out through the primary opening. By performing fistuloscopy of the fistula, the primary opening can be accurately identified. Also, certain fistula treatment methods of the invention include a fistula cleaning step that is performed prior to implanting a fistula graft. For example, an irrigating fluid can be used to remove any inflammatory or necrotic tissue located within the fistula prior to engrafting the graft device. In certain embodiments, one or more antibiotics are applied to the fistula graft device and/or the soft tissues surrounding the fistula as an extra precaution or means of treating any residual infection within the fistula.

Further, the delivery devices and methods of the present invention can be adapted for delivering fistula grafts into multiple fistula tracts in a given medical procedure. In this context, the term "fistula tract" is meant to include, but is not limited to, a void in soft tissues extending from a primary fistula opening, whether blind-ending or leading to one or more secondary fistula openings, for example, to include what are generally described as simple and complex fistulae. In cases of complex fistulae, for example a horse-shoe fistula, there may be one primary opening and two or more fistula tracts extending from that opening. In such instances, a fistula graft may be delivered to any of the fistula tracts.

All publications and patent applications cited in this specification are herein incorporated by reference as if each individual publication or patent application were specifically and individually indicated to be incorporated by reference. Further, any theory, mechanism of operation, proof, or finding stated herein is meant to further enhance understanding of the present invention, and is not intended to limit the present invention in any way to such theory, mechanism of operation, proof, or finding. While the invention has been illustrated and described in detail in the drawings and foregoing description, the same is to be considered as illustrative and not restrictive in character, it being understood that only selected embodiments have been shown and described and that all equivalents, changes, and modifications that come within the spirit of the inventions as defined herein or by the following claims are desired to be protected.

What is claimed is:

1. A fistula plug delivery apparatus for delivering a fistula plug into a fistula tract, the apparatus comprising:
    a fistula plug that includes a plug body having a column strength and a length of at least 3 cm; and
    a removable delivery device including a delivery member segment that is received in the plug body and effective to increase the column strength of the plug body, the delivery member segment, when so received, extending the length or substantially the length of the plug body, the removable delivery device, when advanced through the fistula tract, effective to deliver the plug body into the fistula tract;
    wherein the removable delivery device has a counterforce member configured to provide a generally even load distribution across a proximal-most end of a plug body proximal portion when the counterforce member is applied thereto; and
    wherein the counterforce member fixedly positioned along the delivery member segment and is arranged to contact the proximal-most end of the plug body proximal portion as the plug body is advanced through the fistula tract.

2. The delivery apparatus of claim 1, wherein the plug body is releasably attached to the removable delivery device.

3. The delivery apparatus of claim 2, wherein the removable delivery device is effective to pull the plug body through the fistula tract.

4. The delivery apparatus of claim 3, wherein the removable delivery device is effective to push the plug body through the fistula tract.

5. The delivery apparatus of claim 1, wherein the plug body has a lumen defined therein and extending from a first plug body surface to a second plug body surface, and wherein the removable delivery device extends through the plug body lumen.

6. The delivery apparatus of claim 5, wherein the removable delivery device has a leading tip configured to remain forward of the plug body when the delivery device is advanced through the fistula tract.

7. The delivery apparatus of claim 6, further comprising a protective sheath positioned around the plug body, wherein the protective sheath is releasably attached to the delivery device leading tip.

8. The delivery apparatus of claim 1, wherein the plug body, independent of the removable delivery device, exhibits a substantially cylindrical shape.

9. The delivery apparatus of claim 8, wherein the plug body, independent of the removable delivery device, is generally straight.

10. A method of using the delivery apparatus of claim 1, comprising:
pushing the fistula plug through a fistula tract of a gastrointestinal fistula having a primary opening in a wall of the alimentary canal with the removable delivery device.

11. The method of claim 10, wherein the counterforce member contacts a proximal-most end of the plug body as the plug body is pushed through the fistula tract.

12. The delivery apparatus of claim 1, wherein the removable delivery device is effective to push the plug body through the fistula tract.

13. The delivery apparatus of claim 1, wherein the plug body is comprised of a remodelable angiogenic material.

14. The delivery apparatus of claim 1, wherein the removable delivery device includes a rigid portion.

15. The delivery apparatus of claim 1, wherein the removable delivery device includes a flexible portion.

16. The fistula plug delivery apparatus of claim 1, wherein the plug body has a length of at least 3 cm to 20 cm.

17. The fistula plug delivery apparatus of claim 1, wherein the plug body has a length ranging from 6 cm to 15 cm.

18. The fistula plug delivery apparatus of claim 1, wherein the delivery member segment, when received in the plug body, has a distal end contacting an end wall within the plug body.

19. The fistula plug delivery apparatus of claim 1, wherein the plug body comprises a tissue ingrowth receptive material.

20. The delivery apparatus of claim 1, wherein the plug body has a diameter from 5 mm to 15 mm.

21. The delivery apparatus of claim 1, wherein the elongate plug body has a diameter from 5 mm to 15 mm.

22. The delivery apparatus of claim 1, further comprising a protective sheath positioned around the plug body.

23. A method of delivering a fistula plug into a fistula tract of a fistula having a primary opening in a wall of an alimentary canal, the method comprising:
providing a fistula plug delivery apparatus, the apparatus comprising:
a fistula plug including a plug body having a column strength; and
a removable delivery device received in the plug body and effective to increase the column strength of the plug body, the removable delivery device,
when so received, effective to deliver the plug body into the fistula tract; and
advancing the removable delivery device through the fistula tract of a fistula having a primary opening in a wall of the alimentary canal, wherein the plug body is delivered into the fistula tract in the absence of a protective sheath.

24. The method of claim 23, wherein the plug body has a length of at least 3 cm.

25. The method of claim 24, wherein the plug body has a length of at least 3 cm to 20 cm.

26. The method of claim 23, wherein the plug body has a longitudinal axis and a plug body lumen and includes a transverse wall portion that is transverse to the longitudinal axis of the plug body and is at a plug body proximal portion, and wherein the removable delivery device has a longitudinal axis and includes a transverse delivery surface that is transverse to the longitudinal axis of the removable delivery device and is located proximal of a distal end of the removable delivery device, or wherein the transverse wall portion of the plug body is at a distal terminus of the plug body lumen and wherein the transverse delivery surface of the removable delivery device is at a distal end of the removable delivery device;
wherein the removable delivery device is sized and configured for receipt in the plug body lumen and said transverse delivery surface abuts the transverse wall portion of the plug body; and
wherein advancing the removable delivery device through the fistula tract with the transverse delivery surface abutting the transverse wall portion of the plug body is effective to force the plug body along in the fistula tract.

27. The method of claim 23, wherein a portion of the plug body is positioned forward of the removable delivery device as the removable delivery device is advanced through the fistula tract.

28. The method of claim 23, wherein the plug body has a length ranging from 6 cm to 15 cm.

29. The method of claim 23, wherein the plug body is comprised of a tissue ingrowth receptive material.

30. The method of claim 23, wherein the plug body has a length and the removable delivery device, when received in the plug body, includes a portion extending the length or substantially the length of the plug body.

31. The method of claim 23, wherein advancing the removable delivery device through the fistula tract is effective to pull the plug body through the fistula tract.

32. The method of claim 23, wherein no portion of the plug body is positioned forward of the removable delivery device as the removable delivery device is advanced through the fistula tract.

33. A fistula plug delivery apparatus for delivering a fistula plug into a fistula tract, comprising:
an elongate plug body comprised of a tissue ingrowth receptive material and having a length of at least 1 inch, the elongate plug body having a distal end; and
a removable delivery device that includes a delivery member segment received in the elongate plug body with a distal end of the delivery member segment contacting an end wall at or near the distal end of the elongate plug body, the delivery member segment, while received in the elongate plug body, deliverable to a fistula tract for lodging the elongate plug body in the fistula tract, and the delivery member segment, once delivered to the fistula tract, removable from the elongate plug body without dislodging the elongate plug body from the fistula tract;
wherein the end wall at or near the distal end of the elongate plug body comprises a reinforcing material that is different than the tissue ingrowth receptive material of the elongate plug body proximal of said end wall and prevents the distal end of the removable delivery device from piercing through the end wall during delivery of the fistula plug into the fistula tract.

34. The fistula plug delivery apparatus of claim 33, wherein the elongate plug body has a length of at least 3 cm.

35. The fistula plug delivery apparatus of claim 34, wherein the elongate plug body has a length of at least 3 cm to 20 cm.

36. The fistula plug delivery apparatus of claim 33, wherein the elongate plug body is comprised of an extracellular matrix material.

37. The fistula plug delivery apparatus of claim 36, wherein the extracellular matrix material comprises submucosa, serosa, pericardium, dura mater, peritoneum, or dermal collagen.

38. The fistula plug delivery apparatus of claim 33, wherein the elongate plug body has a length ranging from 6 cm to 15 cm.

39. The fistula plug delivery apparatus of claim 33, wherein the elongate plug body has a lumen defined therein and extending from a plug body surface, and wherein the delivery member segment is received in the plug body lumen.

40. The fistula plug delivery apparatus of claim 33, wherein the delivery member segment includes a rigid portion.

41. The fistula plug delivery apparatus of claim 33, wherein the delivery member segment includes a non-rigid portion.

42. The fistula plug delivery apparatus of claim 33, wherein the delivery member segment is comprised of a naturally derived biocompatible material.

43. The fistula plug delivery apparatus of claim 33, wherein the delivery member segment is comprised of a resorbable material.

44. The fistula plug delivery apparatus of claim 33, wherein the delivery member segment is comprised of a non-naturally derived biocompatible material.

45. The fistula plug delivery apparatus of claim 33, wherein a portion of the elongate plug body is positioned forward of the delivery member segment.

46. The fistula plug delivery apparatus of claim 33, wherein said distal end of said delivery member segment contacts an end wall within a distal segment of the elongate plug body.

47. The fistula plug delivery apparatus of claim 33, wherein the delivery member segment is received in a passage of the elongate plug body, and wherein the passage, independent of the delivery member segment, has a constant diameter along its length.

48. The fistula plug delivery apparatus of claim 33, wherein the delivery member segment is received in a passage of the elongate plug body, and wherein the passage, independent of the delivery member segment, is generally straight.

49. The fistula plug delivery apparatus of claim 33, wherein the elongate plug body includes a generally conical portion.

50. The fistula plug delivery apparatus of claim 33, wherein the elongate plug body is comprised of a rolled sheet-form material.

51. The fistula plug delivery apparatus of claim 33, wherein the elongate plug body is comprised of a synthetic polymeric material.

* * * * *